US010736522B2

United States Patent
Liao et al.

(10) Patent No.: US 10,736,522 B2
(45) Date of Patent: Aug. 11, 2020

(54) METHOD AND TERMINAL FOR OBTAINING FETAL HEART

(71) Applicant: Edan Instruments, Inc., Shenzhen, Guangdong (CN)

(72) Inventors: Weita Liao, Shenzhen (CN); Juanjuan Tan, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 547 days.

(21) Appl. No.: 15/518,163

(22) PCT Filed: Dec. 23, 2016

(86) PCT No.: PCT/CN2016/111677
§ 371 (c)(1),
(2) Date: Apr. 10, 2017

(87) PCT Pub. No.: WO2017/124880
PCT Pub. Date: Jul. 27, 2017

(65) Prior Publication Data
US 2018/0042500 A1  Feb. 15, 2018

(30) Foreign Application Priority Data
Jan. 22, 2016  (CN) .......................... 2016 1 0046562

(51) Int. Cl.
*A61B 5/024*  (2006.01)
*A61B 8/02*  (2006.01)
(Continued)

(52) U.S. Cl.
CPC .......... *A61B 5/02411* (2013.01); *A61B 5/024* (2013.01); *A61B 8/00* (2013.01);
(Continued)

(58) Field of Classification Search
CPC ... A61B 5/02411; A61B 5/024; A61B 5/0011; A61B 5/4343; A61B 8/00; A61B 8/02; A61B 8/0866
See application file for complete search history.

(56) References Cited

U.S. PATENT DOCUMENTS 4,898,179 A * 2/1990 Sirota ...................... A61B 7/04
381/67
2005/0267376 A1  12/2005 Marossero et al.
(Continued)

FOREIGN PATENT DOCUMENTS

CN  102164544 A  8/2011
CN  103169498 A  6/2013
(Continued)

OTHER PUBLICATIONS

International Search Report dated Mar. 24, 2017 for corresponding Chinese Application No. 201610046562.9, filed Jan. 22, 2016.

*Primary Examiner* — Catherine M Voorhees
*Assistant Examiner* — Roland Dinga
(74) *Attorney, Agent, or Firm* — Westman, Champlin & Koehler, P.A.

(57) ABSTRACT

A method for obtaining fetal heart rate which includes: transmitting an ultrasonic pulse wave (110) towards an abdomen of a pregnant woman according to a preset period; receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate (130); outputting the fetal heart rate (150) when a difference value between the fetal heart rate and the pulse rate of the pregnant woman is not lower than a preset threshold. Furthermore, a system and an apparatus for obtaining fetal heart rate are also provided.

(Continued)

The method and terminal for obtaining a fetal heart rate improves accuracy of the obtained fetal heart rate.

10 Claims, 4 Drawing Sheets

(51) Int. Cl.
    *A61B 8/00*           (2006.01)
    *A61B 8/08*           (2006.01)
    *A61B 5/00*           (2006.01)

(52) U.S. Cl.
    CPC .............. *A61B 8/02* (2013.01); *A61B 8/0866* (2013.01); *A61B 5/0011* (2013.01); *A61B 5/4343* (2013.01)

(56) References Cited

U.S. PATENT DOCUMENTS

| | | | |
|---|---|---|---|
| 2012/0179046 A1* | 7/2012 | Kabakov | A61B 5/02411 600/453 |
| 2012/0232398 A1* | 9/2012 | Roham | A61B 8/0866 600/453 |
| 2018/0317878 A1* | 11/2018 | Wohlschlager | A61B 8/02 |

FOREIGN PATENT DOCUMENTS

| | | |
|---|---|---|
| CN | 104382618 A | 3/2015 |
| CN | 204410837 U | 6/2015 |

\* cited by examiner

METHOD AND TERMINAL FOR OBTAINING FETAL HEART

CROSS-REFERENCE TO RELATED APPLICATION

This Application is a Section 371 National Stage Application of International Application No. PCT/CN2016/111677, filed Dec. 23, 2016, which claims priority to Chinese Patent Application No. 201610046562.9, filed Jan. 22, 2016, and in English, the contents of which are hereby incorporated by reference in their entirety.

FIELD OF THE INVENTION

Embodiments of the present application belong to the technical field of medical apparatuses, especially to a method and a terminal for obtaining a fetal heart rate.

BACKGROUND OF THE INVENTION

In a labor stage of a pregnant woman, it is necessary to perform a further process according to an obtained fetal heart rate so as to realize clinical fetal monitoring. Because in the labor stage, uterine contraction of the pregnant woman makes fetal echo weak, accuracy of the obtained fetal heart rate is relatively low. Especially in a second stage of the labor, the uterine contraction of the pregnant woman is severe, and in a time interval when the uterine contraction occurs and a time interval after the uterine contraction, what a fetal heart probe has detected is pulse echo reflected from an abdominal artery or an umbilical artery of the pregnant woman. A result calculated according to the pulse echo is a pulse of the pregnant woman, which means that data output under this circumstance may be a fetal heart rate or a pulse rate of the pregnant woman. Furthermore, because in the second stage of the labor, the pregnant woman would move strenuously for the pain of the uterine contraction, the pulse rate the pregnant woman is generally high at this time; especially when the pulse rate of the pregnant woman is about 110 bpm, the pulse rate of the pregnant woman is prone to be misunderstood as the fetal heart rate, thereby resulting in that the obtained fetal heart rate is indeed invalid data.

In order to solve the above problem, the prior art generally adopts a photoelectric sensor built in a probe, which obtains a fetal heart rate and synchronously calculates the pulse rate of the pregnant woman according to light intensity received by the photoelectric sensor. Then the fetal heart rate and the pulse rate of the pregnant woman would be compared to determine whether the obtained fetal heart rate is valid data.

However, there exist the following deficiencies in the prior art:

the photoelectric sensor is prone to be affected by factors such as ambient light and movements of the pregnant woman, which may result in that the accuracy of the obtained pulse rate of the pregnant woman is low. During the uterine contraction of the pregnant woman, whether an accurate fetal heart rate is detected is especially important, however, the prior art generally cannot detect the pulse rate of the pregnant woman during uterine contraction;

Since the accuracy of the pulse rate of the pregnant woman obtained by the prior art is low, and under special conditions, such as uterine contraction, the pulse rate of the pregnant woman may be even unable to be obtained, when the fetal heart rate is compared with the pulse rate of the pregnant woman, and whether the obtained fetal heart rate is valid date is judged according to the comparison result, it may result in that the accuracy of the obtained fetal heart rate is low too. Therefore, the prior art is still unable to provide an effective determination criterion on whether the fetal heart rate is correct.

SUMMARY OF THE INVENTION

Based on this, it's necessary to provide a method for obtaining a fetal heart rate so as to solve the problem that the prior art is unable to provide an effective determination criterion on whether the fetal heart rate is correct.

Furthermore, it's necessary to provide a system for obtaining fetal heart rate so as to solve the problem that the prior art is unable to provide an effective determination criterion on whether the fetal heart rate is correct.

In order to solve the above problems, technical solutions as follows are adopted.

A method for obtaining fetal heart rate, which includes steps of:

transmitting an ultrasonic pulse wave towards an abdomen of a pregnant woman according to a preset period;

receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate;

outputting the fetal heart rate when a difference value between the fetal heart rate and the pulse rate of the pregnant woman is not lower than a preset threshold; and sending a prompt and outputting the fetal heart rate when the difference value between the fetal heart rate and the pulse rate of the pregnant woman is lower than the preset threshold.

Furthermore, the method for obtaining fetal heart rate further includes presetting duration of the ultrasonic pulse wave.

Furthermore, the step of receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate includes:

receiving a corresponding pulse echo at a first preset time interval after the time of sending the ultrasonic pulse wave in each of the periods, and processing the pulse echo to obtain the corresponding pulse rate of the pregnant woman;

receiving a corresponding fetal heart echo at a second preset time interval after the time of sending the ultrasonic pulse wave in each of the periods, and processing the fetal heart echo to obtain the corresponding fetal heart rate; wherein, the second preset time interval is longer than the first preset time interval.

Furthermore, the method further includes:

stopping receiving and processing the corresponding pulse echo at a third preset time interval after the time of sending the ultrasonic pulse wave in each of the periods;

stopping receiving and processing the corresponding fetal heart echo at a fourth preset time interval after the time of sending the ultrasonic pulse wave in each of the periods; wherein, the third preset time interval is shorter than corresponding second preset time interval.

Furthermore, in the step of transmitting an ultrasonic pulse wave towards an abdomen of a pregnant woman according to a preset period, the ultrasonic pulse wave has two beams, which are respectively a first ultrasonic pulse wave and a second ultrasonic pulse wave;

Correspondingly, the step of receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate includes:

receiving a pulse echo corresponding to the first ultrasonic pulse wave in each of the periods, and processing the pulse echo to obtain a corresponding pulse rate of the pregnant woman;

receiving a fetal heart echo corresponding to the second ultrasonic pulse wave in each of the periods, and processing the fetal heart echo to obtain a corresponding fetal heart rate.

Furthermore, the frequency of the first ultrasonic pulse wave is higher than the frequency of the second ultrasonic pulse wave.

Furthermore, the method further includes:

When the difference value between the fetal heart rate and the pulse rate of the pregnant woman is lower than the preset threshold, displaying a judgment result that the difference value between the fetal heart rate and the pulse rate of the pregnant woman is lower than the preset threshold so as to remind that the fetal heart rate is invalid data.

Furthermore, the method further includes:

when the difference value between the fetal heart rate and the pulse rate of the pregnant woman is lower than the preset threshold, adjusting parameters of the ultrasonic pulse wave corresponding to the fetal heart echo and/or adjusting parameters configured to monitor the fetal heart echo.

Furthermore, adjusting parameters of the ultrasonic pulse wave corresponding to the fetal heart echo includes: increasing the power of the ultrasonic pulse wave corresponding to the fetal heart echo and/or increasing the duration of the ultrasonic pulse wave corresponding to the fetal heart echo; adjusting parameters configured to monitor the fetal heart echo includes: increasing the second time interval and/or increasing the difference value between the fourth preset time interval and the corresponding second preset time interval.

On another aspect, the present application provides a terminal which includes:

an input device, an output device and a processor;

the output device is configured to transmit an ultrasonic pulse wave towards an abdomen of a pregnant woman according to a preset period;

the processor is configured to receive a pulse echo and a fetal heart echo corresponding to the ultrasonic pulse wave at each of the periods through the input device, and respectively process the pulse echo and the fetal heart echo to obtain a corresponding pulse rate of the pregnant woman and fetal heart rate;

the output device is further configured to output the fetal heart rate when the difference value between the fetal heart rate and the pulse rate of the pregnant woman is not lower than a preset threshold.

Furthermore, the processor is further configured to:

receive a corresponding pulse echo at a first preset time interval after time of sending the ultrasonic pulse wave per period, process the pulse echo to obtain a corresponding pulse rate of the pregnant woman, and receive a corresponding fetal heart echo at a second preset time interval after time of sending the periodic ultrasonic pulse wave per period, and process the fetal heart echo to obtain a corresponding fetal heart rate; wherein the second preset time interval is longer than the first preset time interval.

The processor presets duration of the ultrasonic pulse wave.

Furthermore, in the output device, the ultrasonic pulse wave has two beams, which are separately a first ultrasonic pulse wave and a second ultrasonic pulse wave.

Correspondingly, the processor is configured to receive a pulse echo corresponding to the first ultrasonic pulse wave per period through the input device and process the pulse echo to obtain a corresponding pulse rate of the pregnant woman, and configured to receive fetal heart echo corresponding to the second ultrasonic pulse wave per period through the input device and process the fetal heart echo to obtain a corresponding fetal heart rate.

Furthermore, the terminal further includes:

A displayer configured to display a judgment result that the difference value between the fetal heart rate and the pulse rate of the pregnant woman is lower than the preset threshold when the difference value between the fetal heart rate and the pulse rate of the pregnant woman is lower than the preset threshold so as to remind that the fetal heart rate is invalid data.

As can be known from the above technical solutions, the method for obtaining a fetal heart rate obtains a corresponding pulse rate of the pregnant woman and a reference fetal heart rate respectively through the pulse echo and the fetal heart echo, and when the difference values between the reference fetal heart rate and the pulse rate of the pregnant woman is lower than the preset threshold, the reference fetal heart rate is deemed as an actual fetal heart rate, thereby obtaining the fetal heart rate. On one hand, since the method for obtaining the reference fetal heart rate is identical with the method for obtaining pulse rate of the pregnant woman, errors brought by different obtaining methods themselves can be avoided; on the other hand, the pulse rate of the pregnant woman calculated according to the pulse echo is not affected by external factors such as ambient light and probe coupling agent, thereby possessing a higher accuracy. Therefore, the method improves the accuracy of the obtained fetal heart rate, thereby providing high-quality reference data for clinical fetal monitoring which is processed further based on the fetal heart rate.

DETAILED DESCRIPTION OF THE PREFERRED EMBODIMENT

In order to make the purpose, technical solutions and advantages of the present application clearer, the present application will be further described in detail in accompany with the drawings and embodiments. It should be understood that the embodiments described herein are only for explaining the present application, which should be deemed as limiting the present application.

In the embodiments of the present application, ultrasonic pulse wave is transmitted towards an abdomen of the pregnant woman according to a preset period; a pulse echo and a fetal heart echo corresponding to the ultrasonic pulse wave in each of the periods are received; the pulse echo and the fetal heart echo are processed independently to obtain a corresponding pulse rate and the pregnant woman and the fetal heart rate. When the difference value between the fetal heart rate and the pulse rate of the pregnant woman is lower than a preset threshold, the fetal heart rate is output.

Figure 1:
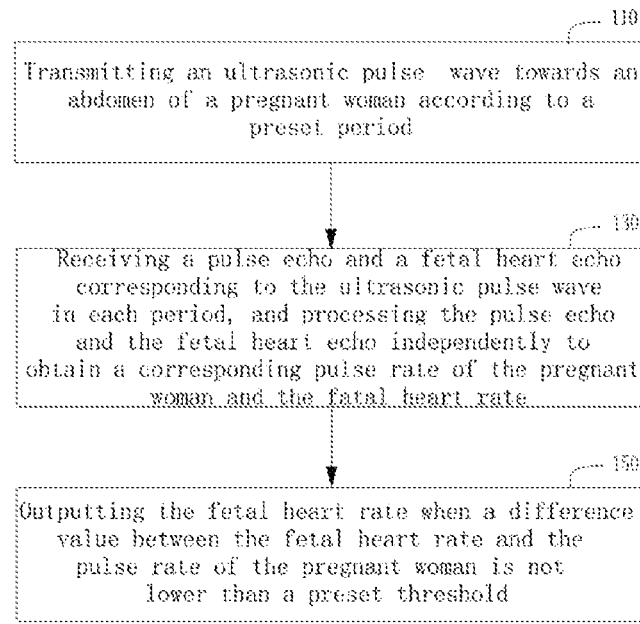
FIG. 1 is a flow chart of a method for obtaining a fetal heart rate in one embodiment.

In order to illustrate the technical solutions of the present application, specific embodiments will be described below:

FIG. 1 is a flow chart of a method for obtaining a fetal heart rate in one embodiment, which is described in detail as follows:

Step 110: transmitting an ultrasonic pulse wave towards an abdomen of a pregnant woman according to a preset period.

Abdominal arteries of the pregnant woman beat obviously and strongly, and the rhyme is synchronous with the pulse of a radial artery; corresponding pulse rate of the pregnant woman can be obtained by monitoring the beat of the abdominal arteries of the pregnant woman.

Because the to-be-monitored fetal heart is located inside the abdomen of the pregnant woman, the ultrasonic pulse wave transmitted towards the abdomen of the pregnant woman can arrive not only to the abdominal arteries of the pregnant woman, but also to the fetal heart inside the abdomen of the pregnant woman. It can also be seen that the same pregnant woman has different pulse monitoring depths and fetal heart monitoring depths. Furthermore, because abdominal skin and tissue depths of each pregnant woman are different, depths of abdominal arteries and depths of fetal heart inside the abdomens of different pregnant women are different, which means that pulse monitoring depths and fetal heart monitoring depths of different pregnant women are also different.

During each of the periods, the transmitted ultrasonic pulse wave would last for a preset duration. Therefore, even though different pregnant women have different pulse monitoring depths or different fetal heart monitoring depths; it can be also ensured that more accurate echo can be obtained during reception.

Step 130: receiving a pulse echo and fetal heart echo corresponding to the ultrasonic pulse wave in each of the periods, and processing the pulse echo and the fetal heart echo independently to obtain a corresponding pulse rate of the pregnant woman and the fetal heart rate.

When the ultrasonic pulse wave reaches the abdominal arteries of the pregnant woman, a pulse echo corresponding to the ultrasonic pulse wave would be returned; similarly, when the ultrasonic pulse wave reaches the fetal heart inside the abdomen of the pregnant woman, a fetal heart echo corresponding to the ultrasonic pulse wave would be returned.

Step 150: outputting the fetal heart rate when a difference value between the fetal heart rate and the pulse rate of the pregnant woman is not lower than a preset threshold.

Specifically, assuming that the preset threshold is 5 bpm, when the difference value between the fetal heart rate and the pulse rate of the pregnant woman is not lower than 5 bpm, the fetal heart rate is output, thereby obtaining the fetal heart rate. Optionally, when the difference value between the fetal heart rate and the pulse rate of the pregnant woman is lower than 5 bpm, a prompt will be sent and the fetal heart rate will be output.

In the above implementation process, the method for obtaining fetal heart rate receives and processes Doppler echoes of different depths, i.e., the pulse echo and the fetal heart echo, so as to obtain the pulse rate of the pregnant woman and the fetal heart rate respectively through calculation, and then output a fetal heart rate based on the comparison and determination result between the fetal heart rate and the pulse rate of the pregnant woman. Because the fetal heart rate is determined through the ultrasonic pulse wave, the fetal heart rate is not affected by ambient light and coupling agent on the fetal heart probe, and the interferences brought by severe movements of the pregnant woman for uterine contraction is reduced significantly, thereby improving the accuracy of the obtained fetal heart rate. It should be noted that the purpose of the present application is to improve the accuracy of the obtained fetal heart rate by the implementation of the above process, however, how to utilize the obtained fetal heart rate to implement further processing and thereby obtain any monitoring result in clinical fetal monitoring are not discussed or limited in the present application.

Figure 2:
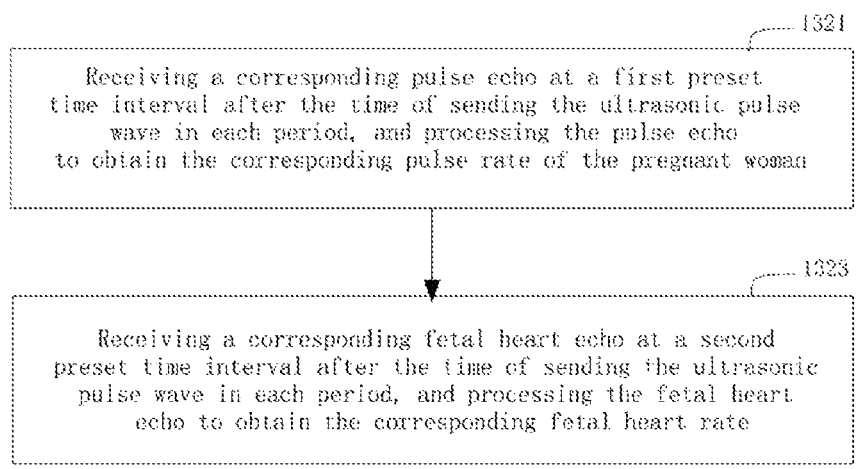
FIG. 2 is a flow chart of steps of receiving a corresponding pulse echo and a fetal heart echo according to an ultrasonic pulse wave in every period, and processing the pulse echo and the fetal heart echo independently to obtain a corresponding pulse rate of a pregnant woman and a fetal heart rate in one embodiment.

As shown in FIG. 2, in another embodiment, the step 130 includes:

Step 1321: receiving corresponding pulse echo at a first preset time interval after time of sending the ultrasonic pulse wave in each of the periods, and processing the pulse echo to obtain a corresponding pulse rate of the pregnant woman; specifically, within a period, if a time during which the ultrasonic pulse wave is sent has reached the first time interval, the corresponding pulse echo is received; otherwise, no corresponding pulse echo is received. For example, assuming that the first time interval is 0.1 second, then corresponding pulse echo is received at 0.1 second after the ultrasonic pulse wave is transmitted.

Step 1323: receiving a corresponding fetal heart echo at a second preset time interval after the time of sending the ultrasonic pulse wave in each of the periods, and processing the fetal heart echo to obtain a corresponding fetal heart rate.

Since the distance that takes the ultrasonic pulse wave to the abdominal arteries of the pregnant woman is shorter than that to the fetal heart, the second preset time interval is longer than the first preset time interval.

Specifically, the first preset time interval is the time during which the ultrasonic pulse wave arrives at and returns from the abdominal arteries of the pregnant woman, which can be obtained by twice the distance that takes the ultrasonic pulse wave to the abdominal arteries of the pregnant woman divided by an average transmitting speed (about 1540 m/s) of the ultrasonic pulse wave in human issues.

The second preset time interval is the time during which the ultrasonic pulse wave arrives at and returns from the fetal heart inside the abdomen of the pregnant woman, which can be obtained by twice the distance that takes the ultrasonic pulse wave to the fetal heart divided by an average transmitting speed of the ultrasonic pulse wave in the human issues.

Figure 3:
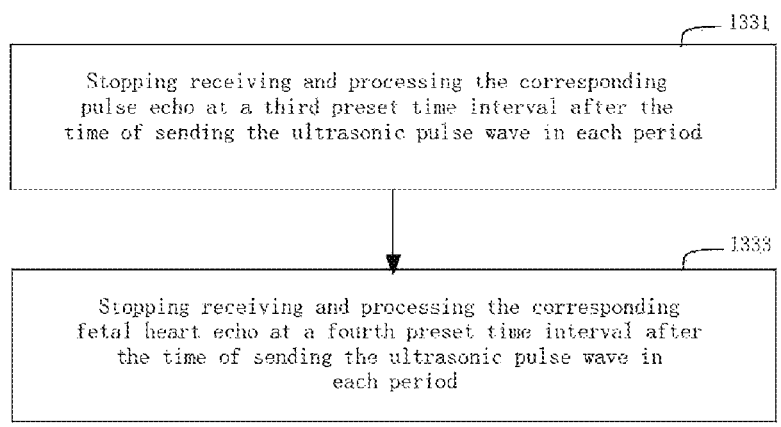
FIG. 3 is a flow chart of receiving a corresponding pulse echo and a fetal heart echo according to an ultrasonic pulse wave in every period, and processing the pulse echo and the fetal heart echo independently to obtain a corresponding pulse rate of a pregnant woman and a fetal heart rate in another embodiment.

As shown in FIG. 3, in another embodiment, the step 130 further includes:

Step 1331, stopping receiving and processing the corresponding pulse echo at a third preset time interval after the time of sending the ultrasonic pulse wave in each of the periods; specifically, within a period, if a time interval during which the ultrasonic pulse wave is sent has reached a third time interval, receiving and processing of the corresponding pulse echo is stopped.

Step 1333, stopping receiving and processing corresponding pulse echo at a fourth preset time interval after the time of sending the ultrasonic pulse wave in each of the periods.

Since the distance that takes the ultrasonic pulse wave to the abdominal arteries of the pregnant woman is much shorter than that to the fetal heart, the third preset time interval is shorter than corresponding second preset time interval. Therefore, the condition that the receiving and processing of the fetal heart echo start before the receiving and processing of the pulse echo are finished would never happen.

For convenience of description, the difference value between the third preset time interval and the corresponding first preset time interval is referred to as a pulse demodulation time, and the difference value between the fourth preset time interval and the corresponding second preset time interval is referred to as a fetal heart demodulation time.

Figure 4:
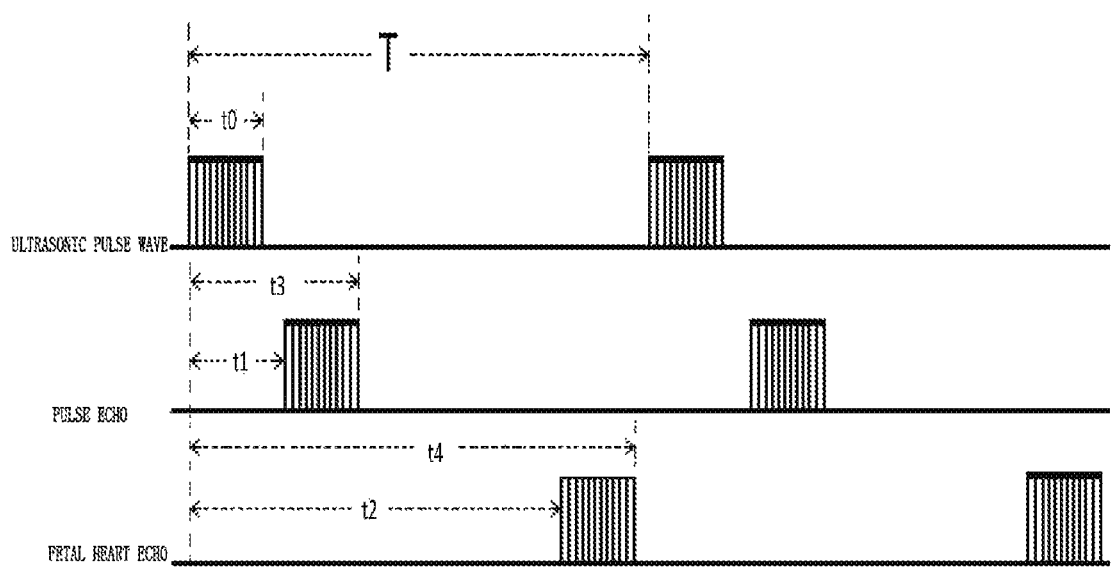
FIG. 4 is a schematic view of a working wave in one embodiment.

In an embodiment as shown by FIG. 4, only one beam of an ultrasonic pulse wave will be transmitted in each preset period T; duration of the ultrasonic pulse wave is represented by t0. It should be noted that FIG. 4 only presents one transmitting sequence; actually, the transmitting sequence of the pulse echo and the fetal heart echo can be changed, which would not be further described herein.

Correspondingly, in step 130, a corresponding pulse echo is received at a first preset time interval t1 after the time of sending the ultrasonic pulse wave in each of the periods, and is ceased to be received at a third preset time interval t3 after the time of sending the ultrasonic pulse wave in each of the periods; a corresponding fetal heart echo is received at a second preset time interval t2 after the time of sending the ultrasonic pulse wave in each of the periods, and is ceased to be received at a fourth preset time interval t4 after the time of sending the ultrasonic pulse wave in each of the periods.

This method can control the transmission of the ultrasonic pulse wave more easily, however, it may be difficult to distinguish and control sensitivity problems brought by the difference between a pulse monitoring depth and a fetal heart monitoring depth.

In another embodiment, in step 110, an ultrasonic pulse wave has two beams, which are respectively a first ultrasonic pulse wave and a second ultrasonic pulse wave. Specifically, a fifth preset time interval, which is a difference value between the second ultrasonic pulse wave and the first ultrasonic pulse wave, is shorter than the preset period but longer than the third preset time interval.

Figure 5:
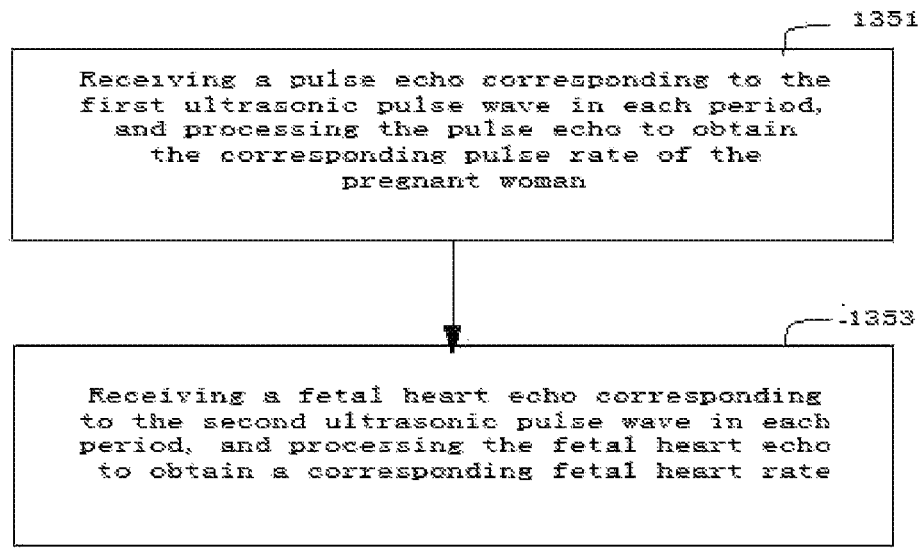
FIG. 5 is a flow chart of receiving a corresponding pulse echo and a fetal heart echo according to an ultrasonic pulse wave in every period, and processing the pulse echo and the fetal heart echo independently to obtain a corresponding pulse rate of a pregnant woman and a fetal heart rate in another embodiment.

Correspondingly, as shown in FIG. 5, the step 130 includes: Step 1351, receiving a pulse echo corresponding to the first ultrasonic pulse wave in each of the periods, and processing the pulse echo to obtain a corresponding pulse rate of the pregnant woman.

Step 1353, receiving a fetal heart echo corresponding to the second ultrasonic pulse wave in each of the periods, and processing the fetal heart echo to obtain a corresponding fetal heart rate.

Figure 6:
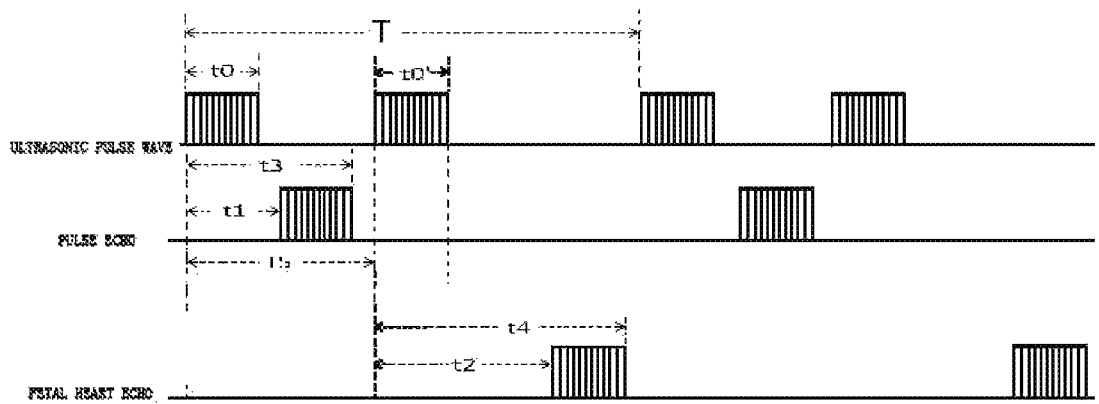
FIG. 6 is a schematic view of a working wave in another embodiment.

In an embodiment as shown by FIG. 6, two beams of the ultrasonic pulse wave will be transmitted in each preset period T; the first ultrasonic pulse wave is only used to monitor the pulse echo, and a duration of the first ultrasonic pulse wave is represented by t0; the second ultrasonic pulse wave is only used to monitor the fetal heart echo, and a duration of the second beam of ultrasonic pulse wave is represented by t0'; a time interval between the second ultrasonic pulse wave and the first ultrasonic pulse wave is the fifth preset time interval t5.

Correspondingly, in the step 130, the pulse echo corresponding to the first ultrasonic pulse wave is received at a first preset time interval t1 after the time of sending the first ultrasonic pulse wave in each of the periods, and is ceased to be received at a third preset time interval t3 after the time of sending the first ultrasonic pulse wave in each of the periods; the fetal heart echo corresponding to the second ultrasonic pulse wave is received at a second preset time interval t2 after the time of sending the second ultrasonic pulse wave in each of the periods, and is ceased to be received at a fourth preset time interval t4 after the time of sending the second ultrasonic pulse wave in each of the periods.

This method can adjust exposure dose of the ultrasonic pulse wave (including the power of the ultrasonic pulse wave and the duration of the pulse wave) more conveniently according to the difference between the abdominal artery depth and the fetal heart depth of the pregnant woman, and can even change the frequency of the ultrasonic pulse wave, thereby monitoring the pulse echo and the fetal heart echo more specifically and effectively.

The frequency of the first ultrasonic pulse wave can be equal to or higher than the frequency of the second ultrasonic pulse wave; in another embodiment, the frequency of the first ultrasonic pulse wave is higher than the frequency of the second ultrasonic pulse wave.

Since the distance that takes the ultrasonic pulse wave to the abdominal artery of the pregnant woman is shorter than that to the fetal heart, utilizing the first ultrasonic pulse wave with a higher frequency to monitor the pulse rate of the pregnant woman can obtain a higher resolution; whereas utilizing the second ultrasonic pulse wave with a lower frequency to monitor the fetal heart rate can obtain a less signal energy attenuation.

In another embodiment, the method further includes steps of:

when the difference value between the fetal heart rate and the pulse rate of the pregnant woman is lower than the preset threshold, displaying a judgment result that the difference value between the fetal heart rate and the pulse rate of the pregnant woman is lower than the preset threshold so as to remind that the fetal heart rate calculated according to the fetal echo is invalid data. Surely, those skilled in the art can represent the judgment result in other ways according to actual conditions, for example, using conventional means such as an acoustic and optical indicating method, a display prompt method, printing display, and so on, which are not further described herein.

Furthermore, the fetal heart rate can actually be output and represented constantly according to actual need at the same time, regardless of the difference relationship between the fetal heart rate and the pulse rate of the pregnant woman.

In another embodiment, the method further includes steps of:

when the difference value between the fetal heart rate and the pulse rate of the pregnant woman is lower than the preset threshold, adjusting parameters of the ultrasonic pulse wave corresponding to the fetal heart echo and/or adjusting parameters configured to monitor the fetal heart echo.

After adjusting the parameters of ultrasonic pulse wave corresponding to the fetal heart echo and/or adjusting the parameters configured to monitor the fetal heart echo, then the steps 110 to 150 are executed to recalculate the fetal heart rate and the pulse rate of the pregnant woman. In accordance with the difference value between the recalculated fetal heart rate and the recalculated pulse rate of the pregnant women, it is determined whether the difference value is not lower than the preset threshold. If yes, the adjustment to the parameters is stopped and the fetal heart rate is output; if not, adjustment to the parameters is continued until the difference value between the fetal heart rate and the pulse rate of the pregnant women is not lower than the preset threshold.

Specifically, adjusting the parameters of the ultrasonic pulse wave corresponding to the fetal heart echo can be increasing the power of the ultrasonic pulse wave corresponding to the fetal heart echo and/or increasing the duration of the ultrasonic pulse wave corresponding to the fetal heart echo.

Adjusting the parameters configured to monitor the fetal heart echo can be increasing the second time interval so as to increase the fetal heart monitoring depth; due to fetal movements, the distance that takes the ultrasonic pulse wave to the fetal heart varies, therefore, the distance that takes the ultrasonic pulse wave to the fetal heart can be chosen as a preset distance, and then the fetal heart echo can be received and processed; and/or, Increasing the fetal heart demodulation time, i.e., increasing the difference value between the fourth preset time interval and the corresponding second preset time interval so as to increase the signal energy obtained after demodulation of the fetal heart echo.

When the difference value between the fetal heart rate and the pulse rate of the pregnant woman is lower than the preset threshold, the present method for obtaining the fetal heart rate may not only prompt the user but may also perform self-adjusting; until the difference value between the fetal heart rate and the pulse rate of the pregnant woman is not lower than the preset threshold, the fetal heart rate would be output again, so that intelligence processing capacity is improved.

It should be understood that in the embodiments of the present application, the sequence numbers of each of the processes described above do not imply the order of execution, and the order of execution of the processes should be determined by their functions and inherent logic, and should not form any limitation to the implementation processes of the embodiments of the present application.

Figure 7:
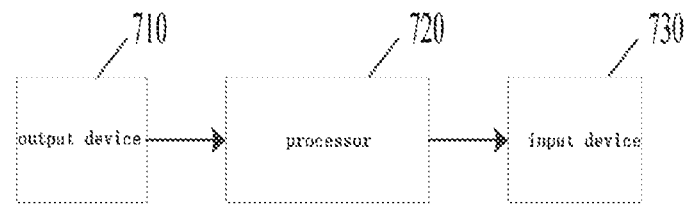
FIG. 7 is a structural schematic view of a terminal in one embodiment.

In an embodiment, in order to solve the above-mentioned problems, a terminal is also provided, as shown in FIG. 7, which includes an output device 710, a processor 720, and an input device 730. Wherein:

the output device 710 is configured to transmit an ultrasonic pulse wave towards a pregnant woman's abdomen according to a preset period, the processor 720 is configured to receive a pulse echo and a fetal heart echo corresponding to the ultrasonic pulse wave at each of the periods through the input device 730, and respectively process the pulse echo and the fetal heart echo to obtain a corresponding pulse rate of the pregnant woman and fetal heart rate;

the output device 710 is further configured to output the fetal heart rate when the difference value between the fetal heart rate and the pulse rate of the pregnant woman is not lower than a preset threshold. Optionally, when the difference value between the fetal heart rate and the pulse rate of the pregnant woman is lower than the preset threshold, prompt information is sent and the fetal heart rate is output.

In another embodiment, the processor 720 is further configured to:

receive a corresponding pulse echo at a first preset time interval after time of sending the ultrasonic pulse wave per period, process the pulse echo to obtain a corresponding pulse rate of the pregnant woman, and receive a corresponding fetal heart echo at a second preset time interval after time of sending the periodic ultrasonic pulse wave, and process the fetal heart echo to obtain a corresponding fetal heart rate; wherein the second preset time interval is longer than the first preset time interval.

The processor presets the duration of the ultrasonic pulse wave.

Specifically, the first time interval and the second time interval are counted by a timer, and a statistical result is fed back to the processor 720.

In another embodiment, the processor 720 is further configured to stop receiving a corresponding pulse echo through the input device 730 and stop processing corresponding pulse echo at a third preset time interval after time of sending the ultrasonic pulse wave at each of the periods and to stop receiving through the input device 730 and stop processing corresponding fetal heart rate at a fourth preset time interval after time of sending the ultrasonic pulse wave at each of the periods; wherein, the third preset time interval is shorter than the second preset time interval.

Figure 8:
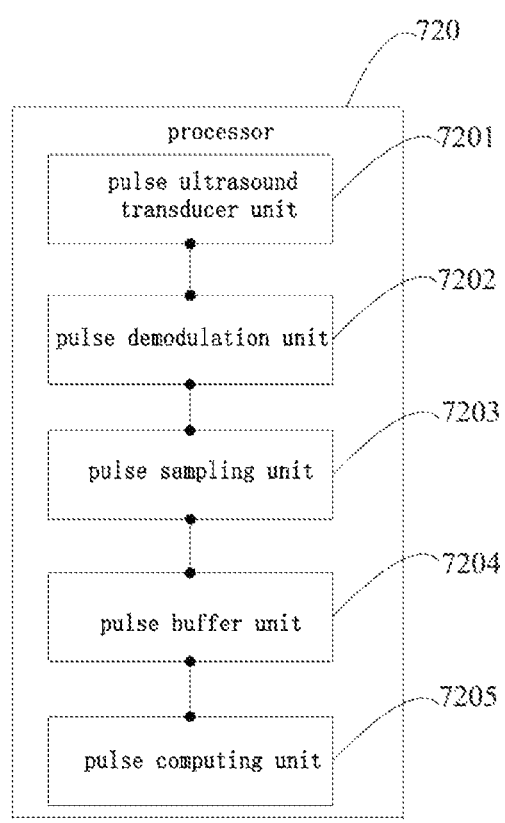
FIG. 8 is a structural schematic view of a processor in one embodiment.

As shown in FIG. 8, in another embodiment, the processor 720 includes a pulse ultrasound transducer unit 7201, a pulse demodulation unit 7202, a pulse sampling unit 7203, a pulse buffer unit 7204, and a pulse computing unit 7205 which are electrically connected in sequence; wherein, the pulse ultrasound transducer unit 7201 is configured to receive a corresponding pulse echo through the input device 730 at a first preset time interval after time of sending the ultrasonic pulse wave per period and to convert the pulse echo to a pulse electric signal; specifically, the ultrasonic transducer unit may be an ultrasonic transducer.

The pulse demodulation unit 7202 is configured to perform a demodulation process on the pulse electric signal to obtain a pulse audio signal.

The pulse sampling unit 7203 is configured to sample the pulse audio signal at a first preset time interval after the time of sending the ultrasonic pulse wave per period to obtain a pulse sampling signal.

The pulse buffer unit 7204 is configured to store the pulse sampling signal.

The pulse computing unit 7205 is configured to calculate a corresponding pulse rate of the pregnant woman based on the stored pulse sampling signal.

Correspondingly, the processor 720 further includes a fetal heart transducer unit, a fetal heart demodulation unit, a fetal heart sampling unit, a fetal heart buffer unit, and a fetal heart computing unit which are sequentially electrically connected.

An envelope of the corresponding pulse audio signal is obtained according to a plurality of stored pulse sampling signals, and the period of the beat of the pregnant woman's abdominal artery is calculated according to the time interval between peak values or valley values of the envelope of the pulse audio signal, and the pulse rate can be further obtained from the period. In addition, the calculation of the fetal heart rate is similar to that of the pulse rate, and would not be further described herein.

Furthermore, the processor 720 further includes a pulse preamplifier unit upstream of the pulse demodulation unit 7202, and a pulse filtering unit and a pulse amplifier unit downstream of the pulse demodulation unit 7202. Correspondingly, a fetal heart preamplifier unit is further included upstream of the fetal heart demodulation unit, and a fetal heart filtering unit and a fetal heart amplifier unit are further included downstream of the fetal heart demodulation unit.

In another embodiment, in the output device 710, the ultrasonic pulse wave has two beams, which are respectively a first ultrasonic pulse wave and a second ultrasonic pulse wave.

Correspondingly, the processor 720 is configured to receive a pulse echo corresponding to the first ultrasonic pulse wave per period through the input device 730 and process the pulse echo to obtain a corresponding pulse rate of the pregnant woman, and configured to receive a fetal heart echo corresponding to the second ultrasonic pulse wave per period through the input device 730 and process the fetal heart echo to obtain a corresponding fetal heart rate.

In another embodiment, the frequency of the first ultrasound pulse wave is higher than the frequency of the second ultrasound pulse wave.

In another embodiment, the terminal further includes:

a reminder configured to display a judgment result that the difference value between the fetal heart rate and the pulse rate of the pregnant woman is lower than the preset threshold when the difference value between the fetal heart rate and the pulse rate of the pregnant woman is lower than the preset threshold so as to remind that the fetal heart rate is invalid data. The reminder can utilize usual acoustic, optical, and electric reminding devices such as display devices, printers, buzzers, etc., which will not be further described herein.

In another embodiment, the processor 720 is further configured to adjust the parameters of the ultrasound pulse wave corresponding to the fetal heart echo and/or adjust the parameters configured to monitor the fetal heart echo when the difference value between the fetal heart rate and the pulse rate of the pregnant woman is lower than the preset threshold.

Specifically, adjusting the parameters of the ultrasonic pulse wave corresponding to the fetal heart echo includes: increasing the power of the ultrasonic pulse wave corresponding to the fetal heart echo and/or increasing the duration of the ultrasonic pulse wave corresponding to the fetal heart echo; adjusting the parameters for monitoring the fetal heart echo includes increasing the second preset time interval and/or increasing the difference value between the fourth preset time interval and the corresponding second preset time interval.

With respect to the circuit configuration of each module in the terminal, a circuit corresponding to the ultrasonic transducer and elements matched with the ultrasonic transducer such as inductances, capacitances, resistances and the like may be arranged in the fetal heart probe, and a circuit corresponding to the other units/modules in the terminal may be arranged in a host that is electrically connected to the fetal heart probe.

Alternatively, besides that the circuit corresponding to the ultrasonic transducer and elements matched with the ultrasonic transducer such as inductances, capacitances, resistances and the like is arranged in the fetal heart probe, a circuit corresponding to the other units in the output device 710 of the terminal, the pulse demodulation unit 7202, the pulse filtering unit, the pulse amplifier unit as well as the fetal heart demodulation unit, the fetal heart filtering unit and the fetal heart amplifier unit in the processor 720 is also arranged in the fetal heart probe, and the circuits corresponding to the other units of the processor 720 is arranged in the host, which means that the pulse audio signal and the fetal heart echo signal are transmitted to the host for the calculation of the pulse rate of the pregnant woman and the fetal heart rate; it is also possible that the circuits corresponding to each module in the terminal are all arranged in the fetal heart probe, which means that the calculation for the pulse rate and the fetal heart rate of the pregnant woman is realized in the fetal heart probe.

In particular, the condition that functions performed on the terminals are integrated in the fetal heart probe facilitates single use of the fetal heart probe; the fetal heart probe is low in power consumption and easy to carry, so that it becomes possible that each pregnant woman can be equipped with an exclusive heart probe. In addition, the fetal heart rate probe can be wirelessly connected with the host, such that the data in all the fetal heart rate probes in use is gathered on the host, which is convenient for unified management of the host.

The pulse pre-amplifier unit and the fetal heart pre-amplifier unit may utilize the same set of circuits, but circuits corresponding to the pulse demodulation unit 7202, the pulse wave filtering unit, the pulse amplifier unit and the fetal heart demodulation unit, the fetal heart filtering unit, and the fetal heart amplifier unit should be divided into two separate sets; otherwise, because the pulse echo and the fetal heart echo obtained at different periods appear alternately, the same set of circuits cannot independently process, for example, demodulate, filter, and amplify, the pulse echo and the fetal heart echo.

By utilizing two individual sets of circuits, only one set of the circuits operate when the pulse echo returns so that the signal output by the pulse demodulation unit 7202, the pulse filtering unit, and the pulse amplifier unit is a complete pulse audio signal; The other set of the circuits work only when the fetal heart echo returns, so that the signal output by the fetal heart demodulation unit, the fetal heart filtering unit, and the fetal heart amplifier unit is a complete fetal heart sound signal.

Correspondingly, the pulse sampling unit 7203 and the fetal heart sampling unit also utilize two separate sets of circuits for sampling the pulse audio signal and the fetal heart audio signal respectively, so as to achieve the purpose of processing the pulse echo and the fetal heart echo separately.

At the same time, the master control unit in the processor 720 controls activation of the pulse demodulation unit 7202 and the fetal heart demodulation unit; the fetal heart sampling unit and the pulse sampling unit 7203 respectively at the first preset time interval and the second preset time interval after the time of sending the ultrasonic pulse wave in each of the periods, and controls closing of the pulse demodulation unit 7202, the fetal heart demodulation unit; the pulse sampling unit 7203 and the fetal heart sampling unit respectively at the third preset time interval and the fourth preset time interval after the time of sending the ultrasonic pulse wave in each of the periods.

Those skilled in the art should understand that the exemplary units and algorithm steps described in accompany with the embodiments disclosed in the specification can be achieved by electronic hardware, or the combination of computer software with electronic hardware. Whether these functions are executed in a hardware manner or a software manner depends on the specific applications and design constraint conditions of the technical solutions. With respect to each specific application, a professional technician can achieve the described functions utilizing different methods, and these achievements should not be deemed as going beyond the scope of the invention.

Those skilled in the art can clearly understand that for convenience and briefness, the specific working process of the described system, apparatus and unit can refer to the corresponding process of the aforementioned method embodiment, which would be further described herein.

It should be understood that the systems, devices and methods disclosed in several embodiments provided by the present application can be achieved in alternative ways. For example, the described device embodiments are merely schematically. For example, the division of the units is merely a division based on logic function, whereas the units can be divided in other ways in actual realization; for example, a plurality of units or components can be grouped or integrated into another system, or some features can be omitted or not executed. Furthermore, the shown or discussed mutual coupling or direct coupling or communication connection can be achieved by indirect coupling or communication connection of some interfaces, devices or units in electric, mechanical or other ways.

The units described as isolated elements can be or not be separated physically; an element shown as a unit can be or not be physical unit, which means that the element can be located in one location or distributed at multiple network units. Some or all of the units can be selected according to actual needs to achieve the purpose of the schemes of the embodiments.

Furthermore, each functional unit in each embodiment of the present invention can be integrated into a processing unit, or each unit can exist in isolation, or two or more than two units can be integrated into one unit.

If the integrated unit is achieved in software functional unit and sold or used as an independent product, the integrated unit can be stored in a computer-readable storage medium. Based on this consideration, the substantial part, or the part that is contributed to the prior art of the technical solution of the present invention, or some or all of the technical solutions can be embodied in a software product. The computer software product is stored in a storage medium, and includes several instructions configured to enable a computer device (can be a personal computer, device, network device, and so on) to execute all or some of the steps of the method of each embodiment of the present invention. The storage medium includes a U disk, a mobile hard disk, a read-only memory (ROM, Read-Only Memory), a random access memory (RAM, Random Access Memory), a disk or a light disk, and other various mediums which can store program codes.

The above contents are merely specific embodiments of the present invention; however, the protection scope of the present invention should not be limited by this. Any person skilled in the art can easily envisage alternations and displacements within the technical scope disclosed by the invention, which should also be within the protection scope of the present invention. Therefore, the protection scope of the present invention should be subject to the protection scope of the claims.

What is claimed is:

1. A method for obtaining fetal heart rate, wherein the method comprises:
    transmitting an ultrasonic pulse wave towards an abdomen of a pregnant woman according to a period;
    receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate;
    outputting the fetal heart rate when a difference value between the fetal heart rate and the pulse rate of the pregnant woman is not lower than a preset threshold.

2. The method for obtaining fetal heart rate of claim 1, wherein the step of receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate comprises:
    receiving a corresponding pulse echo at a first preset time interval after the time of sending the ultrasonic pulse wave in each of the periods, and processing the pulse echo to obtain the corresponding pulse rate of the pregnant woman;
    receiving a corresponding fetal heart echo at a second preset time interval after the time of sending the ultrasonic pulse wave in each of the periods, and processing the fetal heart echo to obtain the corresponding fetal heart rate; wherein,
    the second preset time interval is longer than the first preset time interval.

3. The method for obtaining fetal heart rate of claim 2, wherein, the method further comprises:
    stopping receiving and processing the corresponding pulse echo at a third preset time interval after the time of sending the ultrasonic pulse wave in each of the periods;
    stopping receiving and processing the corresponding fetal heart echo at a fourth preset time interval after the time of sending the ultrasonic pulse wave in each of the periods; wherein,
    the third preset time interval is shorter than corresponding second preset time interval.

4. The method for obtaining fetal heart rate of claim 3, wherein the method further includes:
    when the difference value between the fetal heart rate and the pulse rate of the pregnant woman is lower than the preset threshold, adjusting parameters of the ultrasonic pulse wave corresponding to the fetal heart echo and/or adjusting parameters configured to monitor the fetal heart echo;
    adjusting parameters of the ultrasonic pulse wave corresponding to the fetal heart echo includes: increasing the power of the ultrasonic pulse wave corresponding to the fetal heart echo and/or increasing the duration of the ultrasonic pulse wave corresponding to the fetal heart echo;
    adjusting parameters configured to monitor the fetal heart echo includes: increasing the second time interval and/or increasing the difference value between the fourth preset time interval and the corresponding second preset time interval.

5. The method for obtaining fetal heart rate of claim 1, wherein in the step of transmitting an ultrasonic pulse wave towards an abdomen of a pregnant woman according to a period, the ultrasonic pulse wave has two beams, which are respectively a first ultrasonic pulse wave and a second ultrasonic pulse wave;

correspondingly, the step of receiving a pulse echo and a fetal heart echo corresponding to the ultrasonic pulse wave in each of the periods, and processing the pulse echo and the fetal heart echo independently to obtain a corresponding pulse rate of the pregnant woman and the fetal heart rate comprises:

receiving a pulse echo corresponding to the first ultrasonic pulse wave in each of the periods, and processing the pulse echo to obtain the corresponding pulse rate of the pregnant woman;

receiving a fetal heart echo corresponding to the second ultrasonic pulse wave in each of the periods, and processing the fetal heart echo to obtain a corresponding fetal heart rate.

6. The method for obtaining fetal heart rate of claim 1, wherein the method further comprises:

when the difference value between the fetal heart rate and the pulse rate of the pregnant woman is lower than the preset threshold, displaying a judgment result that the difference value between the fetal heart rate and the pulse rate of the pregnant woman is lower than the preset threshold so as to remind that the fetal heart rate is invalid data.

7. A terminal, wherein the terminal comprises:

an input device, an output device and a processor;

the output device is configured to transmit an ultrasonic pulse wave towards an abdomen of a pregnant woman according to a period;

the processor is configured to receive a pulse echo and a fetal heart echo corresponding to the ultrasonic pulse wave in each of the periods through the input device, and respectively process the pulse echo and the fetal heart echo to obtain a corresponding pulse rate of the pregnant woman and fetal heart rate;

the output device is further configured to output the fetal heart rate when the difference value between the fetal heart rate and the pulse rate of the pregnant woman is not lower than a preset threshold.

8. The terminal of claim 7, wherein the processor is further configured to:

receive a corresponding pulse echo at a first preset time interval after time of sending the ultrasonic pulse wave in each of the periods, process the pulse echo to obtain a corresponding pulse rate of the pregnant woman, and receive a corresponding fetal heart echo at a second preset time interval after time of sending the ultrasonic pulse wave in each of the periods, and process the fetal heart echo to obtain a corresponding fetal heart rate; wherein the second preset time interval is longer than the first preset time interval;

the processor presets duration of the ultrasonic pulse wave.

9. The terminal of claim 7, wherein in the output device, the ultrasonic pulse wave has two beams, which are separately a first ultrasonic pulse wave and a second ultrasonic pulse wave;

correspondingly, the processor is configured to receive a pulse echo corresponding to the first ultrasonic pulse wave in each of the periods through the input device and process the pulse echo to obtain the corresponding pulse rate of the pregnant woman, and configured to receive fetal heart echo corresponding to the second ultrasonic pulse wave in each of the periods through the input device and process the fetal heart echo to obtain the corresponding fetal heart rate.

10. The terminal of claim 7, wherein the terminal further comprises:

a displayer configured to display a judgment result that the difference value between the fetal heart rate and the pulse rate of the pregnant woman is lower than the preset threshold when the difference value between the fetal heart rate and the pulse rate of the pregnant woman is lower than the preset threshold so as to remind that the fetal heart rate is invalid data.

* * * * *